United States Patent
Kataoka et al.

(10) Patent No.: US 7,829,657 B2
(45) Date of Patent: Nov. 9, 2010

(54) POLYCATIONICALLY CHARGED POLYMER AND THE USE OF THE SAME AS A CARRIER FOR NUCLEIC ACID

(75) Inventors: Kazunori Kataoka, Tokyo (JP); Keiji Itaka, Tokyo (JP); Nobuhiro Nishiyama, Tokyo (JP); Shigeto Fukushima, Narashino (JP); Woo-Dong Jang, Seoul (KR); Kanjiro Miyata, Tokyo (JP); Masataka Nakanishi, Tokyo (JP); Shunsaku Asano, Tokyo (JP); Naoki Kanayama, Wako (JP)

(73) Assignee: The University of Tokyo, Tokyo (JP)

(*) Notice: Subject to any disclaimer, the term of this patent is extended or adjusted under 35 U.S.C. 154(b) by 306 days.

(21) Appl. No.: 11/884,146

(22) PCT Filed: Feb. 8, 2006

(86) PCT No.: PCT/JP2006/002577

§ 371 (c)(1),
(2), (4) Date: Apr. 11, 2008

(87) PCT Pub. No.: WO2006/085664

PCT Pub. Date: Aug. 17, 2006

(65) Prior Publication Data
US 2008/0249049 A1    Oct. 9, 2008

(30) Foreign Application Priority Data
Feb. 10, 2005  (JP)  ............................. 2005-035233

(51) Int. Cl.
C08G 69/08    (2006.01)
(52) U.S. Cl. .................... 528/310; 528/335; 424/78.29; 424/78.15; 435/106; 435/109; 435/129; 536/24.3

(58) Field of Classification Search ................. 435/333, 435/106, 109, 129; 424/78.27, 78.29, 78.15; 528/310, 335; 536/24.3
See application file for complete search history.

(56) References Cited

U.S. PATENT DOCUMENTS

2001/0000510 A1    4/2001  Sakurai et al.

(Continued)

FOREIGN PATENT DOCUMENTS

EP    0 721 776    7/1996

(Continued)

OTHER PUBLICATIONS

International Search Report dated Mar. 20, 2006 in connection with PCT/JP2006/302577 corresponding to the present U.S. Application.

(Continued)

*Primary Examiner*—Milton I Cano
*Assistant Examiner*—Michael Leonard
(74) *Attorney, Agent, or Firm*—Wenderoth, Lind & Ponack, L.L.P.

(57) ABSTRACT

Disclosed is a composition for the delivery of nucleic acid to target cells or tissues, which comprises a polycationically charged polymer as a carrier of nucleic acid. The polycationically charged polymer is a polymer which may comprise a charged polymer segment having a main chain based on poly (amino acid), polysaccharide, polyester, polyether, polyurethane or vinyl polymer and having, as a side chain, a group of formula —NH—$(CH_2)_a$—$(NH(CH_2)_2)_e$—$NH_2$ (wherein a and e independently denote an integer of 1 to 5) which is connected to the main chain either directly or via a linker. The disclosed composition has low toxicity, and has a high efficiency in introducing nucleic acid into cells.

22 Claims, 7 Drawing Sheets (a)

(b)

U.S. PATENT DOCUMENTS

2002/0082198 A1 6/2002 Sakurai et al.
2004/0253315 A1 12/2004 Ogawa et al.
2007/0059271 A1* 3/2007 Kataoka et al. ............ 424/78.3

FOREIGN PATENT DOCUMENTS

| EP | 1 415 648 | 5/2004 |
|---|---|---|
| JP | 2003-104914 | 4/2003 |
| JP | 2004-352972 | 12/2004 |
| JP | 2005-154768 | 6/2005 |
| WO | 2004/099287 | 11/2004 |
| WO | 2004/105799 | 12/2004 |
| WO | 2005/078084 | 8/2005 |

OTHER PUBLICATIONS

International Preliminary Report on Patentability issued Aug. 14, 2007 in connection with PCT/JP2006/302577 corresponding to the present U.S. Application.

Yemin Liu et al., "New Poly($_D$-glucaramidoamine)s Induce DNA Nanoparticle Formation and Efficient Gene Delivery into Mammalian Cells", J. Am. Chem. Soc., vol. 126, pp. 7422-7423, 2004.

Kanjiro Miyata et al., "Effect of charge density of backbone polycation on the function of non-viral gene carrier", with English abstract, Polymer Preprints, vol. 54, No. 1, p. 2205, May 2005.

Nobuhiro Nishiyama et al., "Preparation, characterization and biological significance of PEG-*b*-PET block catiomers as efficient synthetic vectors", with English abstract, Polymers Preprints, vol. 54, No. 1, p. 2206, May 2005.

C. F. Bennett et al., "Structural Requirements for Cationic Lipid Mediated Phosphorothioate Oligonucleotides Delivery to Cells in Culture.", Journal of Drug Targeting, vol. 5, No. 3, pp. 149-162, 1997.

Otmane Boussif et al., "A versatile vector for gene and oligonucleotide transfer into cells in culture and in vivo: Polyethylenimine.", Proc. Natl. Acad. Sci., vol. 92, USA, pp. 7297-7301, Aug. 1995.

Simon C. W. Richardson et al., "Potential of low molecular mass chitosan as a DNA delivery system: biocompatability, body distribution and ability to complex and protect DNA.", International Journal of Pharmaceutics, vol. 178, pp. 231-243, 1999.

Neuse et al., "Water-soluble polyamides as potential drug carriers, II", *Die Angewandte Makromolekulare Chemie*, 181 (1990), pp. 153-170 (Nr. 3085).

Neuse et al., "Water-soluble polyamides as potential drug carriers", *Die Angewandte Makromolekulare Chemie*, 192 (1991), pp. 35-50 (Nr. 3300).

* cited by examiner

POLYCATIONICALLY CHARGED POLYMER AND THE USE OF THE SAME AS A CARRIER FOR NUCLEIC ACID

This application is a U.S. National Phase application under 35 U.S.C. §371 of PCT Application No. PCT/JP06/02577, filed Feb. 8, 2006, which claims priority under 35 U.S.C. §119 (a)-(d) of Japanese Patent Application No. 2005 035233, filed Feb. 10, 2005.

TECHNICAL FIELD

This invention belongs to a technical field on the delivery of nucleic acid to target cells or tissues, and relates, more specifically, to the use of polycationically charged polymer as a carrier for the delivery of nucleic acid, and also to a novel polycationically charged polymer.

BACKGROUND ARTS

As a means to convey nucleic acid or its analogue to target cells or tissues, there have been made various proposals about both of virus vector and synthetic vector (or non-virus vector) as so-called gene carrier or vector. Synthetic vector is considered to have no grave toxicity as compared with virus vector although synthetic vector is not free of some risk of toxicity or the like as brought into question in drug delivery system which has been studied in conventional medical treatment. Furthermore, in synthetic vector, there is no limitation on the size of nucleic acid to be carried, and, moreover, precise molecular designing is possible. For these reasons, assiduous research and development are being made with regard to synthetic vector. Typical examples of synthetic vector include cationic lipid (e.g., lipofectin) and cationic polymer each of which forms an ion complex with negatively charged DNA. In the former, it has been tried to lower the toxicity against cells by changing the molecular structure of lipid, and also to enhance the efficiency of expression of gene in the introduced cells, and, thus, results have been produced to a certain extent (see, e.g., non-patent document 1. Documents are identified below. The same is applied to other documents.). In vivo, however, desired results have not been obtained.

As for the latter, on the other hand, there have long been studied poly(L-lysine), DEAE-dextran, polyethylenimine (see, e.g., non-patent document 2), chitosan (see, e.g., non-patent document 3), etc. They are, however, still unsatisfactory in toxicity against cells, and also in the efficiency of introduction and expression of gene.

Under the above-mentioned circumstances, the inventors of this invention have found out that the use of block copolymer which is made of cationic polymer (e.g., polylysine) and, connected thereto, water-soluble and low-toxicity polyethylene glycol (PEG) forms polymer micelle which is an autonomously associated polyion complex (PIC) with DNA encapsulated therein. The inventors have thus confirmed that such a polymer micelle lowers toxicity, and shows expression efficiency higher than that of lipofectin which is now being most widely employed for in vitro gene introduction. The inventors have also provided a block copolymer which is composed of a segment chain having a specific amine group at side chain as a cationically charged group and PEG chain, as a block copolymer which may be used as a further improved carrier of gene (see patent document 1: Japanese Patent Application KOKAI Publication No. 2004-352972).

List of Documents:
  Patent document 1: Japanese Patent Application KOKAI Publication No. 2004-352972
  Non-patent document 1: C. F. Benett et al., J. Drug Targeting, 5, 149 (1997)
  Non-patent document 2: O. Boussif et al., Proc. Natl. Acad. Sci., USA, 92, 7297 (1995)
  Non-patent document 3: S. C. Richardson et al., Int. J. Pharm. 178, (1999) 231

DISCLOSURE OF INVENTION

It is, however, still necessary to obtain further various means for nucleic acid delivery. The inventors have found out that a block copolymer as mentioned in patent document 1 which is composed of a segment chain having a specific amine group at side chain as a cationically charged group and of PEG chain is quite low toxic against animal cells (in particular mammalian cells), and is capable of keeping gene which has been introduced into cells in an expressible state for a long period of time, and, that, by these merits, said block copolymer is usable as a carrier or vector by which to maintain the expression of introduced gene for a long period of time without giving adverse effects on cells having, for instance, differentiation potency. The inventors have further found out that such a polymer which has a segment chain having a specific amine group at side chain is, even when it has no PEG chain and does not form polymer micelle as PIC with DNA, quite low toxic against animal cells (in particular mammalian cells), and is capable of keeping gene which has been introduced into cells in an expressible state for a long period of time, in contrast to polycationically charged polymer such as poly(L-lysine), DEAE-dextran, polyethylenimine and chitosan.

Thus, this invention provides a composition for the delivery of nucleic acid to target cells or tissues, which composition comprises polycationically charged polymer as a carrier of nucleic acid. This invention further provides the use of polycationically charged polymer for the preparation of a composition for the delivery of nucleic acid to target cells or tissues. This invention also provides a method for the delivery of nucleic acid to target cells or tissues, which method comprises bringing a conjugate of nucleic acid and polycationically charged polymer into contact with said target cells or tissues.

Polycationically charged polymer which is used in the above is selected from the group consisting of a charged polymer having a main chain based on poly(amino acid), polysaccharide, polyester, polyether, polyurethane or vinyl polymer and having, as a side chain, a group of formula —NH—$(CH_2)_a$—$(NH(CH_2)_2)_e$—$NH_2$ (wherein a and e independently denote an integer of 1 to 5) which is connected to said main chain either directly or via a linker, and a block copolymer made of a segment chain derived from the above-mentioned charged polymer and a segment chain derived from nonionic hydrophilic polymer. When the polycationically charged polymer is a block copolymer, target cells or tissues may be either cells having differentiation potency or tissues which contain said cells. In a preferable embodiment, the above-mentioned nonionic hydrophilic polymer is selected from the group consisting of poly(ethyleneglycol), poly(vinylalcohol), poly(vinylpyrrolidone), poly(methacrylamide), poly(acrylamide), poly(hydroxyethylmethacrylate) and poly(hydroxyethylacrylate).

In a more specific embodiment of invention, polycationically charged polymer is a polymer of formula (III) below or its salt.

wherein $R^{10}$ denotes hydroxyl group, oxybenzyl group or a group of —NH—$R^{11}$ wherein $R^{11}$ denotes unsubstituted or substituted straight chain or branched $C_{1-20}$ alkyl group; $R^{2a}$ and $R^{2b}$ independently denote methylene group or ethylene group; $R^3$ denotes hydrogen atom, protecting group, hydrophobic group or polymerizable group; $R^{5a}$ and $R^{5b}$ independently denote hydroxyl group, oxybenzyl group or a group of —NH—$(CH_2)_a$—X wherein a denotes an integer of 1 to 5, and wherein X independently denote either a residue of amine compound which contains at least one species of primary, secondary, tertiary or quaternary ammonium salt or a residue of compound other than amine, with the proviso that, among the total of $R^{5a}$ and $R^{5b}$, there are at least two —NH—$(CH_2)_a$—X groups wherein X denotes $(NH(CH_2)_2)_e$—$NH_2$ wherein e denotes an integer of 1 to 5; $R^{6a}$ independently denote hydrogen atom or protecting group which is selected from the group consisting of Z-group, Boc-group, acetyl group and trifluoroacetyl group which are usually employed as a protecting group for amino group; n denotes an integer of 2 to 5,000; y denotes an integer of 0 to 5,000; and z denotes an integer of 0 to 5,000, with the proviso that y+z is not larger than n. In the above formula, recurring units are mentioned in a specific order for convenience sake. Actually, however, recurring units may be present in a random order.

In another more specific embodiment of invention, polycationically charged polymer is a block copolymer of formula (I) or (II) below or its salt.

wherein $R^{1a}$ and $R^{1b}$ independently denote hydrogen atom or unsubstituted or substituted straight chain or branched $C_{1-12}$ alkyl group; $L^1$ and $L^2$ each denote a linker; $R^{2a}$, $R^{2b}$, $R^{2c}$ and $R^{2d}$ independently denote methylene group or ethylene group; $R^3$ denotes hydrogen atom, protecting group, hydrophobic group or polymerizable group; $R^4$ denotes hydroxyl group, oxybenzyl group or a group of —NH—$(CH_2)_a$—X or a residue of initiator wherein a denotes an integer of 1 to 5, and wherein X independently denote either a residue of amine compound which contains at least one species of primary, secondary, tertiary or quaternary ammonium salt or a residue of compound other than amine; $R^{5a}$, $R^{5b}$, $R^{5c}$ and $R^{5d}$ independently denote hydroxyl group, oxybenzyl group or a group of —NH—$(CH_2)_a$—X wherein a denotes an integer of 1 to 5, and wherein X independently denote either a residue of amine compound which contains at least one species of primary, secondary, tertiary or quaternary ammonium salt or a residue of compound other than amine, with the proviso that, among the total of $R^{5a}$ and $R^{5b}$ and the total of $R^{5c}$ and $R^{5d}$, there are at least two —NH—$(CH_2)_a$—X groups wherein X denotes $(NH(CH_2)_2)_e$—$NH_2$ wherein e denotes an integer of 1 to 5; $R^{6a}$ and $R^{6b}$ independently denote hydrogen atom or protecting group which is selected from the group consisting of Z-group, Boc-group, acetyl group and trifluoroacetyl group which are usually employed as a protecting group for amino group; m denotes an integer of 5 to 20,000; n denotes an integer of 2 to 5,000; y denotes an integer of 0 to 5,000; and z denotes an integer of 0 to 5,000, with the proviso that y+z is not larger than n. In the above formula, recurring units are mentioned in a specific order for convenience sake. Actually, however, recurring units may be present in a random order.

Furthermore, as far as the inventors know, the polymer of the above-mentioned formula (III) has never been mentioned in any document. Thus, polymer of the above-mentioned formula (III) or its salt is also provided as an embodiment of this invention.

This invention also provides a conjugate of polymer of the above-mentioned formula (III) and nucleic acid.

BRIEF EXPLANATION OF DRAWINGS

FIG. 3 is a fluorescence micrograph in place of drawing, which shows the result of experiment of introduction of GFP gene into primary cultured cell lines in Example 2. Figure (a)

shows the result of introduction into osteoblast strain originated in mouse parietal bones, and Figure (b) shows the result of introduction into synovial fibroblasts from human being.

DETAILED DESCRIPTION OF INVENTION

In the following, this invention is explained in more detail.

Nucleic acid as referred to in this invention means, although not restrictive, any nucleic acid or nucleic acid-related substance that may have some actions or other on animal cells when delivered to them. Classified according to chemical structure, DNA, RNA and nucleic acid analogue of so-called oligo or polymer (e.g., peptide nucleic acid and nucleic acid analogue wherein phosphoric acid part of nucleic acid has been modified into phosphorothioate, methylphosphonate, phosphate trimester, phosphoroamidate, etc.) are included in the nucleic acid of this invention. From the viewpoint of the manner of function, the nucleic acid of this invention includes any molecule that carries genetic information or belongs to the category of antisense.

With regard to polycationically charged polymer, the phrase "having a main chain based on poly(amino acid)" means preferably a main chain of poly(amino acid) which is formed through peptide bond from natural or synthetic amino acids. The phrase "having a main chain based on polysaccharide" means sugar chain such as DEAE-dextran, chitosan or polygalactosamine. The phrase "having a main chain based on vinyl polymer" means polymer chain which is formed by the polymerization of ethylenically unsaturated polymerizable monomer. Side chain means a group of formula —NH—$(CH_2)_a$—$(NH(CH_2)_2)_e$—$NH_2$ (wherein a and e independently denote an integer of 1 to 5) which is connected to said main chain either directly or via a linker. Such a side chain is, when the main chain is based on poly(amino acid), connected to main chain via carboxyl group at β- or γ-position, amino group at ε-position, etc. When the main chain is based on polysaccharide, side chain is connected via hydroxyl group, amino group or carboxyl group in sugar portion. When the main chain is based on vinyl polymer, side chain is connected via hydroxyl group, amide group or carboxyl group of poly (vinyl alcohol), poly(methacrylamide), poly(acrylamide) or poly(methacrylic acid). The connection as mentioned above may be made via a linker having an alkylene chain which has 22 or less carbon atoms, and which may be interrupted with one to ten oxygen or sulfur. Such a side chain is usually introduced by polymer reaction although it is not restrictive. As for the reaction, there is employed halogen-substitution reaction, condensation reaction with use of carboxyl group or amino group, ester exchange reaction or amionlysis. The molecular weight of such a polymer is usually 1,000 to 200,000 although it is not restrictive so long as the purpose of this invention is achieved.

Polycationically charged polymer which is preferably used in this invention is a polymer of formula (III) or its salt, or a block copolymer of formula (I) or (II) or its salt. Salt as referred to in this invention includes, although not restrictive, salts with counter ion such as Cl⁻, Br⁻, I⁻, (½$SO_4$)⁻, $NO_3^-$, (½$CO_3$)⁻, (⅓$PO_4$)⁻, $CH_3COO^-$, $CF_3COO^-$, $CH_3SO_3^-$ and $CF_3SO_3^-$.

Straight chain or branched $C_{1-12}$ denoted by $R^{11}$, $R^{1a}$ and $R^{1b}$ in formula (III), formula (I) or (II) include methyl, ethyl, n-propyl, isopropyl, n-butyl, secbutyl, tert-butyl, n-pentyl, n-hexyl, decyl and undecyl. When the alkyl group is to be substituted, examples of substituent include acetalized formyl group, cyano group, formyl group, carboxyl group, amino group, $C_{1-6}$ alkoxycarbonyl group, $C_{2-7}$ acylamide group, tri (same or different)-$C_{1-6}$ alkylsiloxy group, siloxy group or silylamino group. In the above, the term "acetalized" means the formation of acetal portion by a reaction between carbonyl of formyl and two molecules of alkanol having one to six carbon atoms or alkylenediol which may be branched and has two to six carbon atoms. This is also a means to protect said carbonyl group. When the substituents is an acetalized formyl group for instance, it can be hydrolyzed under acidic mild condition, and converted to formyl group (—CHO or aldehyde group) which is another substituents. Formyl group, carboxyl group or amino group as mentioned above can be used for giving to carrier, via themselves, antibody or its fragment (F(ab')₂, F(ab), etc.) having specific bondability of the antibody, and other functionality or targeting property. Preferably used is a polymer of formula (III) wherein, among the total of $R^{5a}$ and $R^{5b}$, —NH—$(CH_2)_a$—X groups wherein X denotes $(NH(CH_2)_2)_e$—$NH_2$ wherein e denotes an integer of 1 to 5 account for 50% or more. More desirable is a polymer wherein, among the total of $R^{5a}$ and $R^{5b}$, —NH—$(CH_2)_a$—X groups wherein X denotes $(NH(CH_2)_2)_e$—$NH_2$ wherein e denotes an integer of 1 to 5 account for 85% or more.

Also preferable is a polymer wherein all or a part of $R^{5a}$ and $R^{5b}$ are —NH—$(CH_2)_a$—X groups wherein a is 2 and e is 1. Furthermore, a polymer of formula (III) wherein $R^{2a}$ and $R^{2b}$ denote methylene group is preferable.

Desirable in particular is a polymer of formula (III) wherein each group is as mentioned above and wherein X is selected from the group consisting of the following groups:

-continued

—N(CH$_2$CH$_3$)$_2$, —(NR$^{7b}$(CH$_2$)$_{d2}$)$_{e2}$—(NR$^{7c}$(CH$_2$)$_{d3}$)$_{e3}$—NHR$^{8b}$,

—(CH$_2$)$_g$CH$_3$, or wherein X$^2$ denote hydrogen atom, C$_{1-6}$ alkyl group or amino C$_{1-6}$ alkyl group; R$^{7a}$, R$^{7b}$ and R$^{7c}$ independently denote hydrogen atom or methyl group; d1, d2 and d3 independently denote an integer of 1 to 5; e1, e2 and e3 independently denote an integer of 1 to 5; f denotes an integer of 0 to 15; R$^{8a}$ and R$^{8b}$ independently denote hydrogen atom or protecting group which is selected from the group consisting of Z-group, Boc-group, acetyl group and trifluoroacetyl group which are usually employed as a protecting group for amino group; and g denotes an integer of 0 to 15. More especially desirable is a polymer of the same formula wherein z denotes 0 (zero) and/or R$^3$ is selected from the group consisting of acetyl group, acryloyl group and methacryloyl group.

When polycationically charged polymer of this invention is a block copolymer, preferably used is a copolymer of formula (I) or (II) wherein, among the total of R$^{5a}$ and R$^{5b}$ and the total of R$^{5c}$ and R$^{5d}$, —NH—(CH$_2$)$_a$—X groups wherein X denotes (NH(CH$_2$)$_2$)$_e$—NH$_2$ wherein e denotes an integer of 1 to 5 account for 50% or more, or further desirably 85% or more. Also preferable is a polymer wherein all or a part of R$^{5a}$, R$^{5b}$, R$^{5c}$ and R$^{5d}$ are —NH—(CH$_2$)$_a$—X groups wherein a is 2 and e is an integer of 1 to 3, in particular e is 1. More specifically usable is a block copolymer of formula (I) or (II) wherein L$^1$ denotes —(CH$_2$)$_b$—NH— (b denotes an integer of 1 to 5) and L$^2$ denotes —(CH$_2$)$_c$—CO— (c denotes an integer of 1 to 5). Especially preferable is a block copolymer wherein R$^{2a}$, R$^{2b}$, R$^{2c}$ and R$^{2d}$ denote methylene group, and wherein X is selected from the groups which are concretely mentioned above with respect to formula (III).

More desirably usable in this invention is a block copolymer of formula (I) or (II) wherein each group is as defined above, and R$^3$ denotes acetyl group, acryloyl group or methacryloyl group, and, under circumstances, R$^4$ denotes —NH—R$^9$ wherein R$^9$ denotes unsubstituted or substituted straight chain or branched C$_{1-20}$ alkyl group.

In formula (I), (II) or (III), R$^{2a}$, R$^{2b}$, R$^{2c}$ and R$^{2d}$ independently denote methylene group or ethylene group as mentioned above. When both of R$^{2a}$ and R$^{2b}$ denote methylene group, the recurring unit corresponds to poly(aspartic acid derivative). When both denote ethylene group, the recurring unit corresponds to poly(glutamic acid derivative). When, on the other hand, both of R$^{2c}$ and R$^{2d}$ denote methylene group, the recurring unit corresponds to poly(aspartic acid derivative), and when both denote ethylene group, the recurring unit corresponds to poly(glutamic acid derivative). When, in formula (I), (II) or (III), R$^{2a}$ and R$^{2b}$ denote methylene group and ethylene group, and when R$^{2c}$ and R$^{2d}$ denote methylene group and ethylene group, recurring unit of aspartic acid derivative and glutamic acid derivative can exist either in the form of block or at random.

A part of block copolymers as mentioned above are disclosed in the above-mentioned patent document 1, and can be manufactured by the method as mentioned therein or by a modification of the method.

In the composition of this invention, the mixing ratio of nucleic acid and polycationically charged polymer can be expressed by a proportion (N/P ratio) of cation in polymer to phosphoric acid group in nucleic acid molecule. N/P ratio is a quantity defined by the following equation. Thus, N/P ratio hereinafter means this quantity unless otherwise defined.

$$N/P \text{ ratio} = \frac{[\text{Total number of cation in polymer in solution}]}{\begin{bmatrix} \text{Total number of phosphoric acid} \\ \text{group in nucleic acid in solution} \end{bmatrix}}$$

In this invention, N/P ratio is not limited so long as polyion complex is formed. Thus, N/P ratio differs depending on the nature of non-charged segment or charged segment in polymer. Anyone skilled in the art could choose appropriate N/P ratio.

In the preparation of composition, nucleic acid and polymer need to be blended in an aqueous medium, preferably in a medium based on deionized water. Where necessary, there may additionally be performed manipulation such as dialysis, agitation, dilution, condensation, ultrasonic treatment, temperature control, pH control, ionic intensity control and the addition of organic solvent.

In order that the composition of this invention may be delivered to targeted tissues or tissues, the composition and the targeted tissues or tissues have only to be placed in a state where they can be brought into contact with each other. Such a contact may be achieved by the cultivation of cells in the presence of the composition, or by the addition of the composition into culture of cells. Contact of the composition with cells or tissues in vivo, on the other hand, can be attained by the administration of the composition to an individual which needs the introduction of the nucleic acid (or an individual to be treated) by any administration method that is usually employed in the field of genetic therapy. Examples of such an individual include, although not restrictive, human being, mouse, rat, rabbit, dog, monkey, ox, horse, pig, birds, or the like. As for the method of administration, there can be mentioned the direct introduction or implantation into the targeted tissue or in the vicinity of targeted cells or tissue, intravenous injection, intra-arterial injection, intramuscular injection, peroral administration, transpulmonary administration, etc. In such administration, there can be used also diluent, vehicle or other physiologically active components which are usually employed in the field of medicinal formulation. Administration as stated above is capable of curing diseases of the above-mentioned individual such as genetic disease, cancer, refractory diseases like AIDS, infectious diseases, etc.

In the following, this invention is explained in more detail with concrete examples, to which however this invention is not to be restricted.

Production Example 1

Synthesis of poly(N-(2-aminoethyl)-aminoethylaspartamide)

β-Benzyl-L-aspartate-N-carboxylic anhydride (BLA-NCA) was dissolved in a mixed solvent of N,N-dimethylformamide (DMF) and dichloromethane, and was then subjected to polymerization reaction with use of butylamine as an initiator, at 40° C. for two days. After N terminal was acetylated with acetic anhydride, the resultant mixture was subjected to reprecipitation, and then to drying to give poly(β-benzyl-L-aspartate) (PBLA) polymer. PBLA was dissolved in DMF, and, then, diethylenetriamine in an amount of 50-fold equivalent with regard to benzyl ester was added. The resultant mixture was made to react at 40° C. for one day. The resultant reaction liquid was added dropwise to an aqueous solution of acetic acid. The resultant solution was put in a dialysis tube, and, thus, dialysis was conducted with use of 0.01 N hydrochloric acid as an outer liquid. After evaporation, freeze drying was conducted to give white powders of poly (N-(2-aminoethyl)-aminoethylaspartamide. Thus obtained polymer (hereinafter referred to also as DET) was a hydrochloride of polymer of the following structural formula wherein n was 98.

Production Example 2

Synthesis of polyethylene glycol-poly(N-(2-aminoethyl)-aminoethylaspartamide block copolymer

Polyethylene glycol whose one terminal was methoxy and the other terminal was aminopropyl, and whose average molecular weight was 12,000 was dissolved in dichloromethane. To the resultant solution, there was added a solution which had been prepared by dissolving BLA-NCA in a mixed solvent of DMF and dichloromethane. The resultant solution was made to react at 40° C. for two days. Furthermore, N terminal was acetylated with acetic anhydride, and, thus, polyethylene glycol-block-poly(β-benzyl-L-aspartate) (PEG-PBLA) was obtained. From analysis with NMR, the polymerization degree of PBLA portion was known to be 68. In the following, a block copolymer wherein PEG has a molecular weight of 12,000, and wherein PBLA portion has a polymerization degree of 68 may be referred to as PEG-PBLA (12-68) (parenthetically mentioned FIG. 12 stands for molecular weight of 12,000, and 68 stands for polymerization degree). Thus obtained PEG-PBLA (12-68) was dissolved in benzene, and was then subjected to freeze drying. The freeze-dried product was dissolved in DMF in an atmosphere of argon. To the resultant solution, there was added diethylenetriamine, which had been purified by distillation drying, in an amount of 50-fold equivalent with regard to benzyl ester. The resultant mixture was stirred in argon atmosphere at 40° C. for 24 hours. The resultant reaction solution was added dropwise to 10% acetic acid. The resultant solution was dialyzed against 0.1 N hydrochloric acid with use of dialysis membrane having a molecular weight cut off of 3500. The resultant inner liquid was recovered, and was then freeze dried to give white solid of PEG-DET block copolymer in the form of hydrochloride having structural formula (V) below:

Production Example 3

Synthesis of polyethylene glycol-poly(N-(3-aminopropyl)-aminopropylaspartamide block copolymer The same PEG-PBLA (12-68) as used in Production Example 2 was dissolved in benzene, and was then subjected to freeze drying. The freeze-dried product was dissolved in DMF in an atmosphere of argon. To the resultant solution, there was added dipropylenetriamine, which had been purified by distillation drying, in an amount of 50-fold equivalent with regard to benzyl ester. The resultant mixture was stirred in argon atmosphere at 40° C. for 24 hours. The resultant reaction solution was added dropwise to 10% acetic acid. The resultant solution was dialyzed against 0.1 N hydrochloric acid with use of dialysis membrane having a molecular weight cut off of 3500. The resultant inner liquid was recovered, and was then freeze dried to give white solid of PEG-DPT block copolymer in the form of hydrochloride having structural formula (VI) below:

Example 1

Introduction of Gene into Cultured Cells (Cell Lines) with Use of DET and PEG-DET In this Example, the ability of DET and PEG-DET to introduce gene into cells was evaluated by the introduction of luciferase gene into cell lines.

<Material and Method>

A complex of PEG-DET and luciferase gene-encoding plasmid DNA (pDNA) (available from Riken Gene Bank) was prepared by blending PEG-DET solution with PDNA solution at various NIP ratios on the day before transfection, and subsequently leaving the resultant blends to stand overnight. On the other hand, a complex of DET and pDNA was prepared by blending solutions with each other 30 minutes before transfection. Incidentally, N/P ratio as mentioned above is a quantity defined by the following equation. Thus, N/P ratio hereinafter means this quantity unless otherwise defined.

$$N/P \text{ ratio} = \frac{[\text{Total number of cation in polymer in solution}]}{\left[\begin{array}{c}\text{Total number of phosphoric acid} \\ \text{group in nucleic acid in solution}\end{array}\right]}$$

For control, there were used Exgen 500 (linear polyethylenimine, which may hereinafter be abbreviated as LPEI; manufactured by MBI Fermentas) which is one of the best, in gene-introducing ability, among gene-introducing cationic polymer reagents on the market; and also Fugene 6 (Roche) and Lipofectamine (invitrogen) which are lipid-based reagents for gene introduction were used. Exgen 500 was prepared under a condition of N/P=10 under which the highest expression of gene might be shown. Fugene 6 and Lipofectamine were prepared according to manufacturer's protocol.

For the preparation of cells, HuH-7 cells and 293T cells were each seeded in an amount of $2.5\times10^4$ cells/well in a 24-well dish, and were then incubated in 10% serum-containing DMEM for 24 hours, and were thus provided for experiment. Then, medium was replaced with another 10% serum-containing DMEM (250 μl/well). Subsequently, each complex as prepared was added dropwise into the medium, and, thus, transfection was conducted. Each complex was administered in an amount of 0.75 μg/well as pDNA. After 48 hours of incubation in this state, the expression of luciferase gene was quantified.

<Results>

Figure 1:
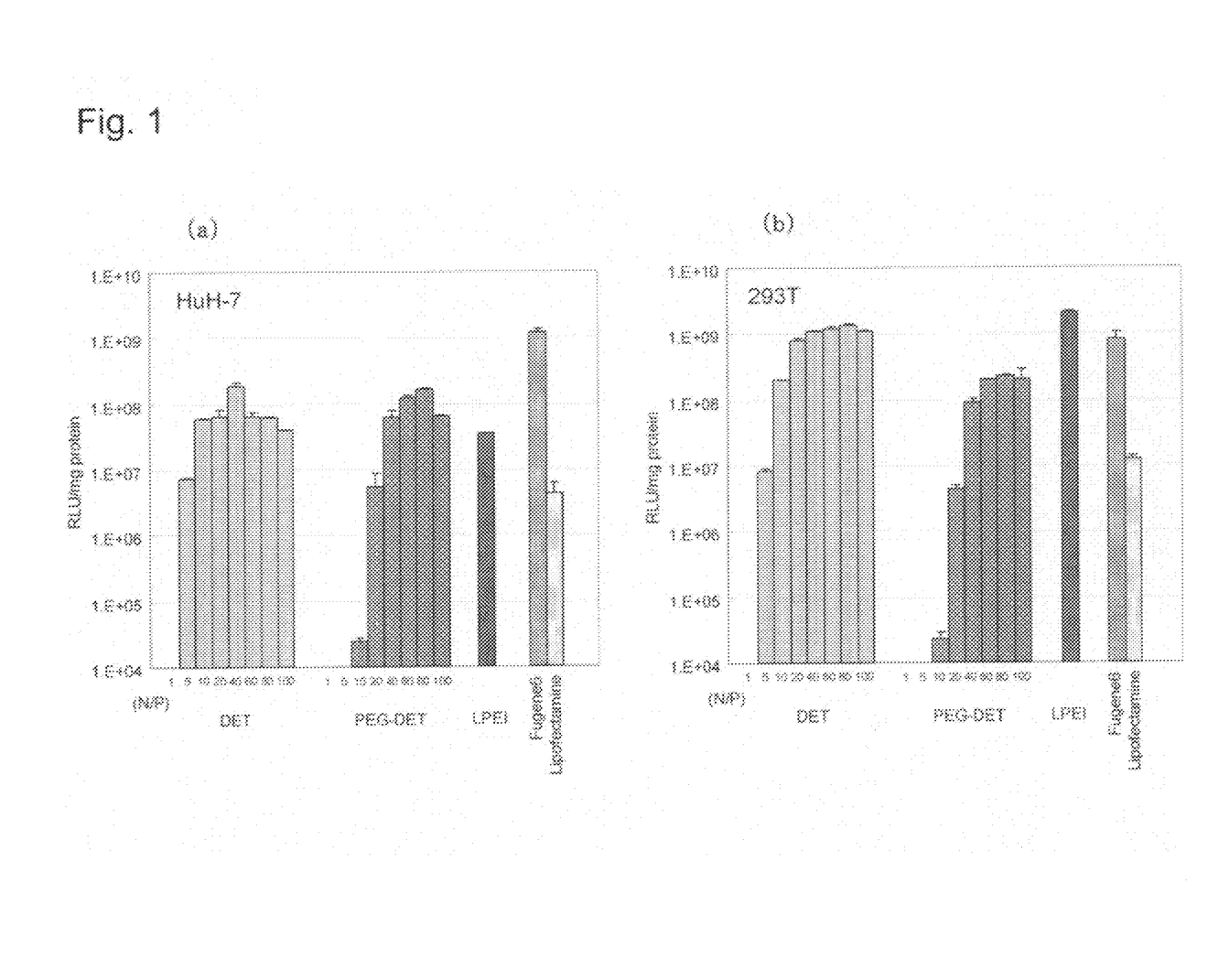
FIG. 1 is a graph which shows the result of expression of luciferase gene in Example 1. Figure (a) corresponds to HuH-7 cells, and Figure (b) corresponds to 293T cells. LPEI indicates the result of linear polyethylenimine (Exgene 500) (the same applies to the following Figures). In this graph, vertical axis shows the amount of luciferase gene expressed, and horizontal axis shows the ratio (N/P) of cation in polymer to phosphoric acid group in DNA.

As shown in FIG. 1, it was confirmed that DET/pDNA complex exhibited high expression of luciferase gene, in particular when N/P ratio was 10 or more, in both of the cells.

As for PEG-DET/pDNA complex, high expression of gene was observed when N/P ratio was 20 or more. In HuH-7 cells, both of the reagents fell short of Fugene 6, but surpassed Exgen 500 in gene expression. In 293T cells, although the same tendency was seen, both slightly fell short of Exgen 500. Furthermore, in both DET and PEG-DET, expression lowered under the condition where N/P ratio was above 80.

Example 2

Introduction of Gene into Primary Cultured Cell Lines with Use of DET and PEG-DET Further, the introduction of gene into primary cultured cell lines was conducted with use of DET and PEG-DET. Generally, it had been hard in most cases to introduce exogenous gene into primary cultured cell lines. One of the reasons is that primary cultured cell lines are susceptible in particular to cytotoxicity of reagent. Polyethylenimine is known to have strong cytotoxicity in spite of good ability of gene introduction, and, thus, polyethylenimine had been difficult to be used for the introduction of gene into primary cultured cell lines.

<Material and Method>

For cells, there were used both primary osteoblasts (POB) taken from parietal bones of one day-old mouse and synovial fibroblasts from human being.

For evaluation by luciferase gene, cells were each seeded in an amount of $2.5\times10^4$ cells/well in a 24-well dish as in Example 1, and were then incubated in 10% serum-containing DMEM for 24 hours, and, then, transfection was conducted. The expression of luciferase gene was quantified after 48 hours and 120 hours (only for synovial fibroblasts).

With regard to PEG-DET and Exgen 500, evaluation was conducted also with use of GFP gene. Cells were each seeded in an amount of $1\times10^5$ cells/well in a 6-well dish, and, after 24 hours of culturing, transfection was conducted. After 48 hours of incubation, the expression of GFP gene was observed with fluorescence microscope.

<Results>

Figure 2:
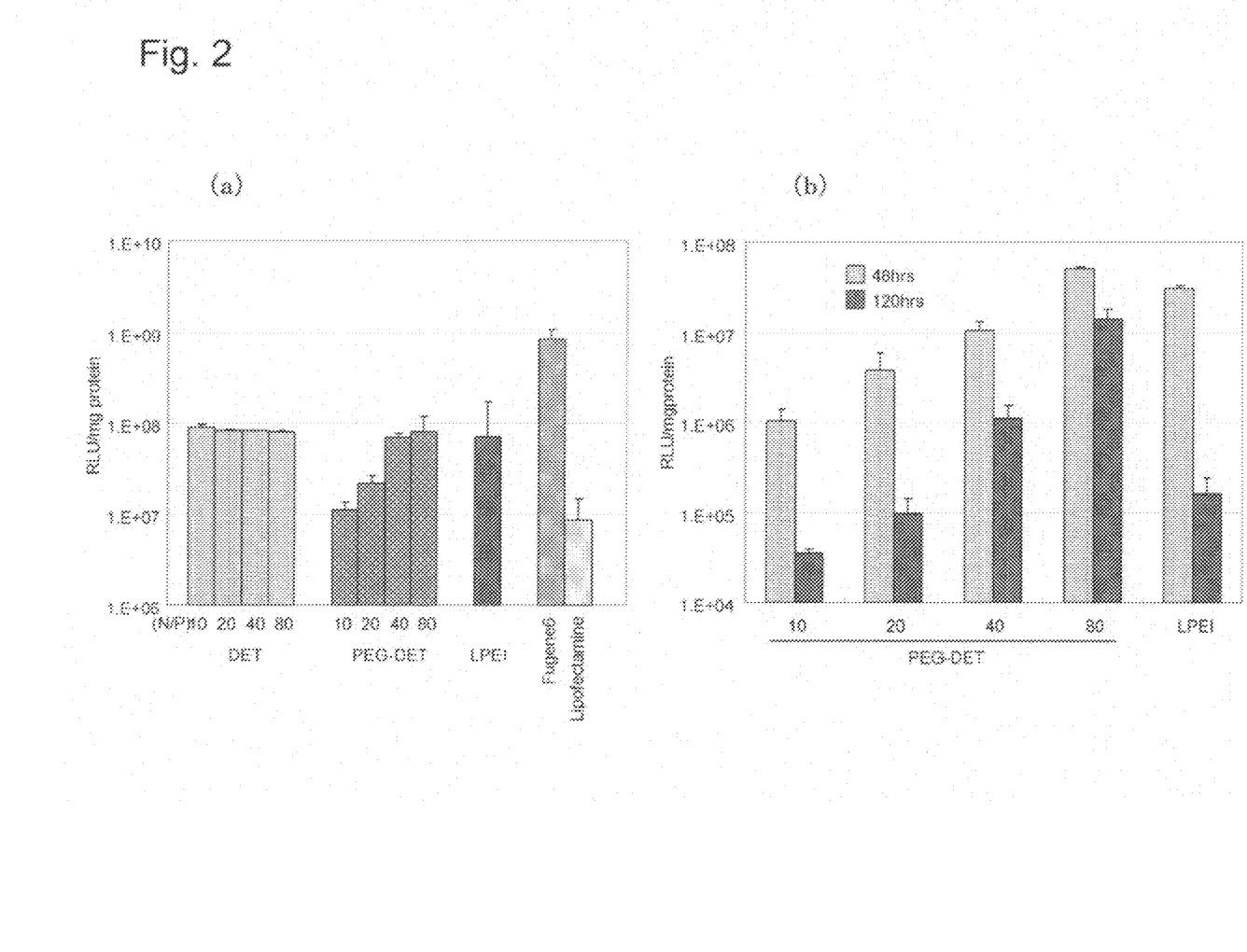
FIG. 2 is a graph which shows the result of experiment of introduction of luciferase gene into primary cultured cell lines in Example 2. Figure (a) shows the result of introduction into osteoblast strain originated in mouse parietal bones, and Figure (b) shows the result of introduction into synovial fibroblasts from human being.
Figure 3:
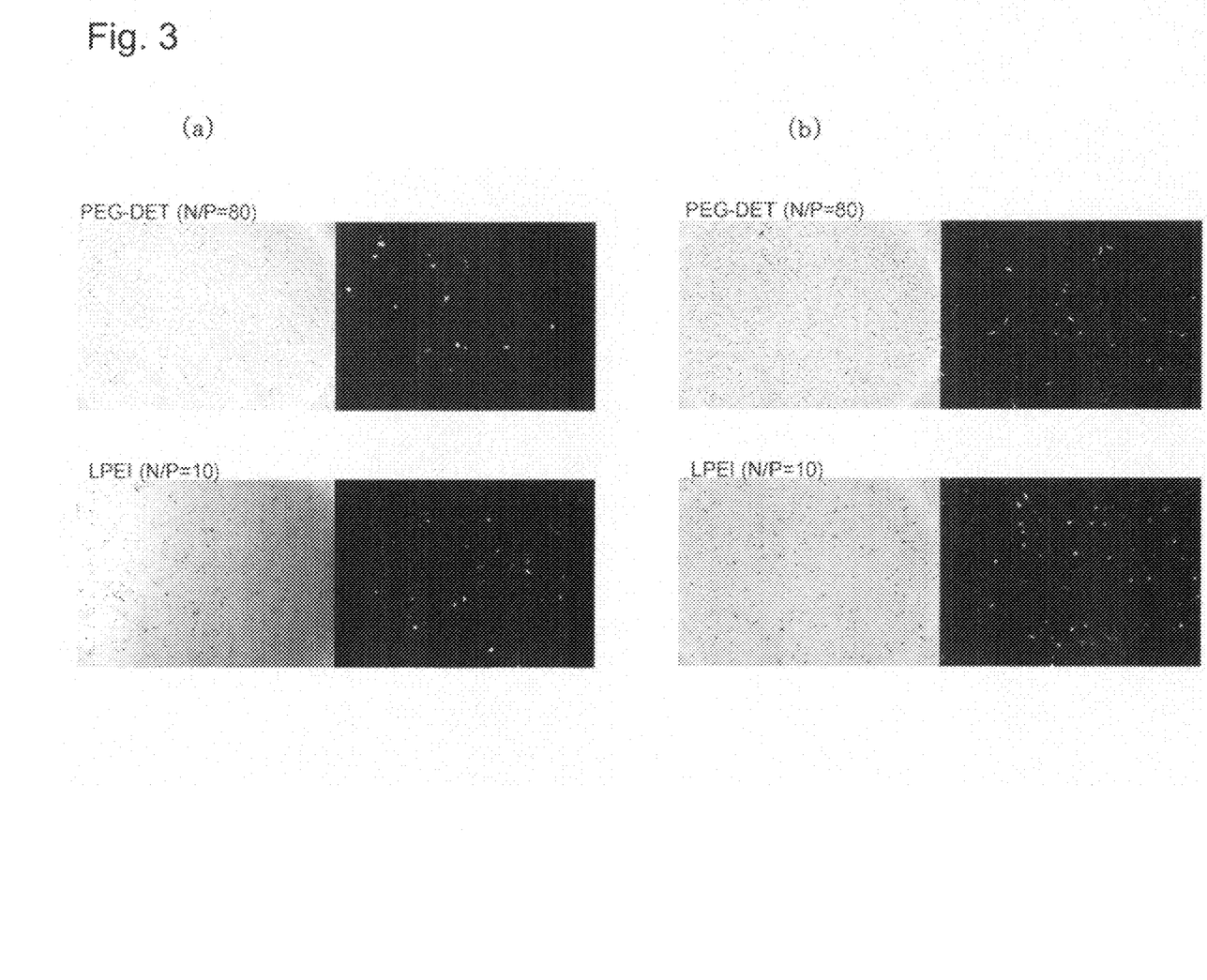

In POB, both PEG-DET and DET achieved good expression for both luciferase gene (FIG. 2) and GFP gene (FIG. 3). In the quantification of luciferase gene, both of the reagents fell short of Fugene 6, but slightly surpassed Exgen 500 in gene expression. Furthermore, what was characteristic is that, as shown in light field image of FIG. 3, PEG-DET brought about no decrease of number of cells, and caused almost no change of the form of cells, as compared with Exgen 500, and, thus, it was suggested that PEG-DET had very low cytotoxicity.

The same tendency was confirmed also in synovial fibroblasts. Whereas, in Exgen 500, there was seen a remarkable decrease of expression after 120 hours from transfection as compared with expression after 48 hours, the change was scanty in PEG-DET. It is considered that this difference in expression was due to the difference in cytotoxicity.

Example 3

Evaluation of Cytotoxicity of DET and PEG-DET

In view of confirming the low cytotoxicity of DET and PEG-DET which had been suggested in the experiment of transfection, the number of living cells after the transfection into primary cultured cell lines was quantified and evaluated with MTT assay.

<Material and Method>

POB and synovial fibroblasts (for PEG-DET alone) were used as in Example 2.

For evaluation by luciferase gene, cells were each seeded in an amount of $8\times10^3$ cells/well in a 96-well dish, and after 24 hours of culturing, transfection was conducted. Thus, the number of living cells after 48 hours was quantified with MTT assay (cell counting kit by Dojindo) (n=8). The result was indicated after standardized by the number of cells of control wherein no transfection had been performed.

<Results>

Figure 4:
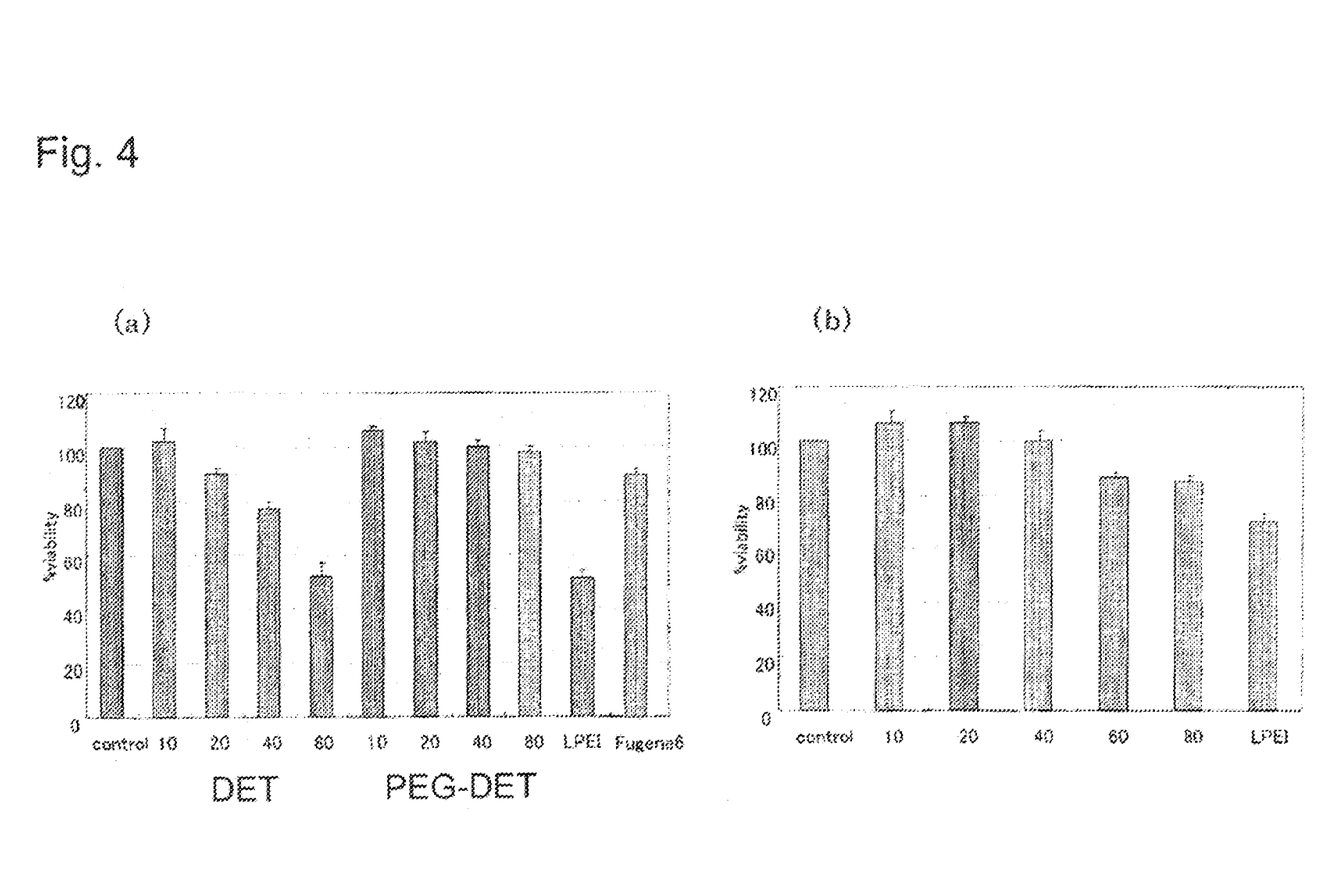
FIG. 4 is a graph which shows the change of number of living cells after transfection into primary cultured cell lines in Example 3. Figure (a) shows the result of transfection into osteoblast strain originated in mouse parietal bones, and Figure (b) shows the result of transfection into synovial fibroblasts from human being.

In PEG-DET, almost no cytotoxicity is seen through N/P=10-80 in both of the cells, as shown in FIG. 4, and, thus, it is confirmed that there was no influence on proliferation. In Exgen 500 (N/P=10), on the other hand, the number of cells remarkably decreased as compared with control, and, thus, it is known that cytotoxicity was very strong in spite of good genetic expression. In DET, although almost no cytotoxicity is seen at N/P=10, the number of cells gradually decreases as N/P ratio rises higher. As stated above, DET achieves very good expression at N/P=10. Thus, it is known that both DET and PEG-DET are polymers which are able to attain good gene introduction so long as cytotoxicity is very low.

Example 4

Application to the Induction of Differentiation of Osteoblasts

DET and PEG-DET were evaluated with respect to differentiation induction caused by the introduction of transcription factor gene into osteoblasts while the function of DET and PEG-DET, i.e., very low toxicity and good gene introduction ability, was made full use of.

<Material and Method>

Runx 2 which is a transcription factor for the differentiation of osteoblasts was introduced into POB with PEG-DET, DET and Fugene 6, and, thus, the expression of osteocalcin which is a marker of the differentiation of osteoblasts was quantified on the $5^{th}$ and the $10^{th}$ days.

For cells, POB was prepared in a 24-well dish as mentioned hereinbefore, and, after 24 hours, pDNA encoding Runx 2 gene was transfected with use of PEG-DET and DET. The preparation of complex was conducted at N/P=80 for PEG-DET, and at N/P=10 for DET. For negative control, there were placed cells which had been cultured without transfection, and cells into which GFP gene-encoding pDNA had been transfected.

<Results>

Figure 5:
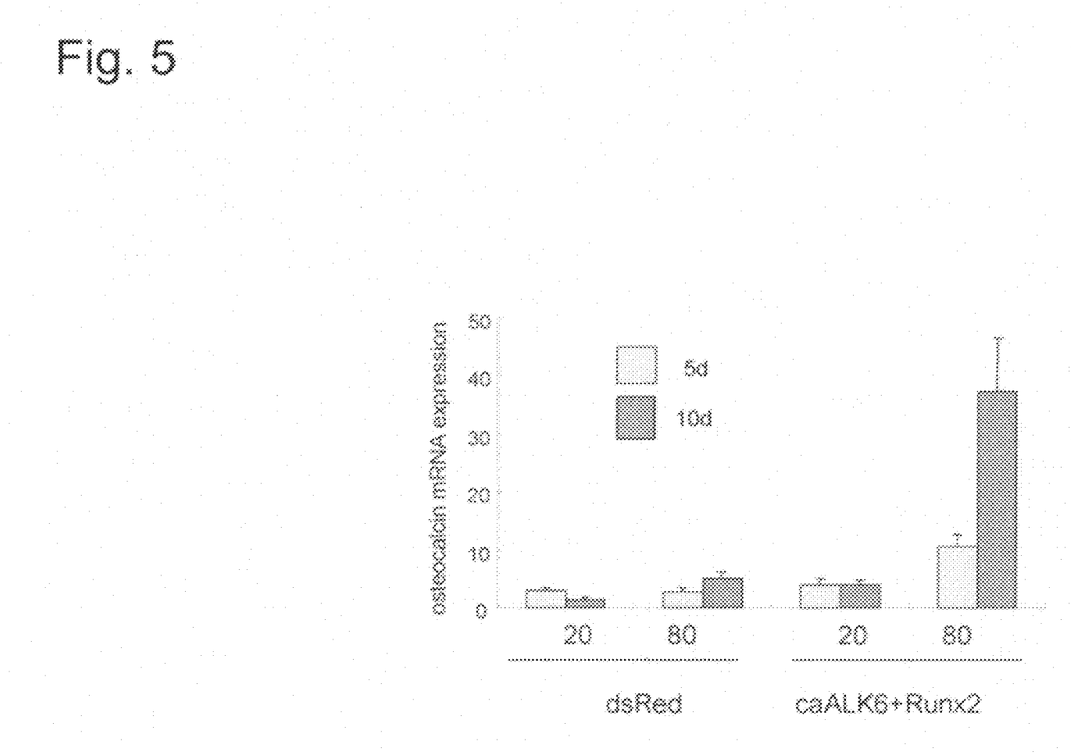
FIG. 5 is a graph which shows the expression of osteocalcin as a marker of differentiation of osteoblasts after the introduction of transcription factor Runx 2 into osteoblast strain (POB) by PEG-DET (N/P=20 or 80) in Example 4. This graph shows the result of quantification of expression of osteocalcin mRNA by real-time PCR on the $5^{th}$ day and the $10^{th}$ day.

As shown in FIG. 5, cells into which Runx 2 had been introduced with PEG-DET and DET exhibited evident acceleration of expression of osteocalcin on the $5^{th}$ day as compared with non-transfection cells, and, on the $10^{th}$ day, the expression was remarkably promoted. Cells into which Runx 2 had been introduced with Fugene 6, on the other hand, exhibited only little expression of osteocalcin. In both of the methods, no difference was seen between cells into which GFP gene had been introduced and non-transfection cells.

Thus, although each of PEG-DET, DET and Fugene 6 exhibited good genetic expression in the evaluation by the introduction of reporter gene such as luciferase gene, GFP gene and the like, Fugene 6 did not achieve good result in the differentiation of osteoblasts by the introduction of Runx 2 whereas PEG-DET and DET attained excellent differentiation induction. This is a very interesting result. As a reason for this result, it was guessed that Fugene 6 had an influence (toxicity) on cells which was not detected in MTT assay or the like, but which might possibly inhibit differentiation. Otherwise, Fugene 6 may be different from PEG-DET and DET in the state of intracellular genetic expression, and this difference may have caused the above-mentioned difference in result. In order to investigate the possibility of the latter mechanism, the following experiment was conducted.

Example 5

Evaluation of Continuous Expression of Gene

Luciferase gene was introduced into POB with the three of PEG-DET, DET and Fugene 6. Resultant genetic expression was evaluated as a usual expression of luciferase gene, i.e., as an amount of expressed luciferase protein, and, simultaneously, the expression of intracellular expression of luciferase mRNA was quantified and evaluated with real-time PCR.

<Material and Method>

Transfection with luciferase gene was conducted in the same manner as in Example 2, and, thus, sample was recovered after 1, 3 and 5 days. Light-emission quantification of the expression of luciferase gene was conducted in the same manner as in Example 2. As for the quantification of mRNA, RNA was extracted from sample cells and purified, and, then, luciferase gene mRNA was quantified with real-time PCR (Applied Biosystems, Prism 7000).

<Results>

Figure 6:
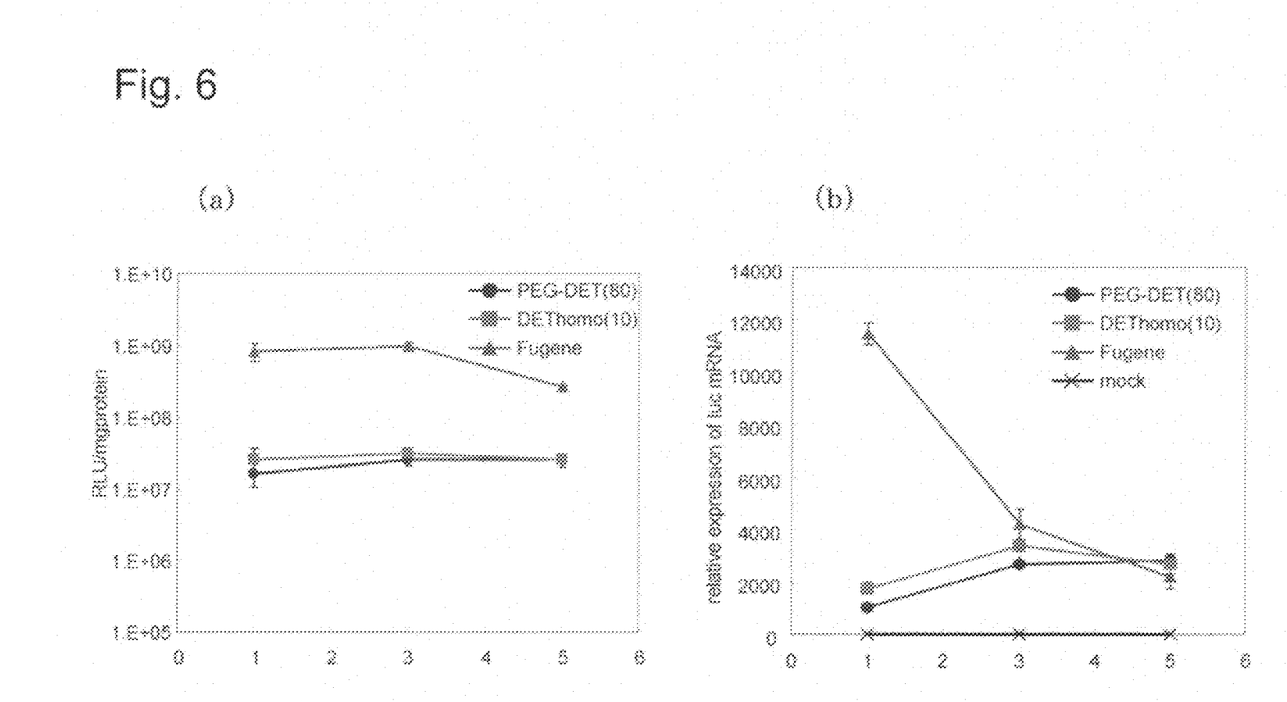
FIG. 6 is a graph which shows the result of continuous expression of luciferase gene in POB in Example 5. Figure (a) shows the expression of luciferase gene as the amount of protein expressed, and Figure (b) shows the change of the amount of luciferase mRNA expressed. Horizontal axis indicates the date of sampling after transfection.

As shown in FIG. 6, emission quantification indicated that Fugene 6 exhibited very high expression from the first day, and that the expression slightly decreased on the $5^{th}$ day. PEG-DET and DET, on the other hand, exhibited relatively low expression, but the expression was comparatively maintained up to the $5^{th}$ day.

This tendency was remarkably seen in evaluation on mRNA level. Fugene 6 exhibited very high expression on the first day, but the expression rapidly lowered on the $3^{rd}$ day. PEG-DET and DET, on the other hand, rather exhibited an increase of expression from the $1^{st}$ to the $3^{rd}$ day, and, on the $5^{th}$ day, the expression slightly surpassed expression by Fugene 6.

Thus, when observed with regard to the expression of luciferase protein, Fugene 6 already exhibited very high expression on the first day. This protein was accumulated in cells, and, resultantly, emission quantification indicated relatively high expression for a long period of time. As for the process of transcription from thus introduced PDNA, on the other hand, new mRNA transcription is considered to cease to occur at a very early stage in Fugene 6 whereas said process of transcription is considered to be kept for as long as several days or more in PEG-DET and DET.

The above-mentioned difference in the pattern of genetic expression may possibly have caused the different results of the induction of cell differentiation. In detail, the following might have been suggested: Temporary expression of transcription factor is insufficient to turn on the differentiation switch; only a system which is capable of the expression of transcription factor for more than several days leads to effective differentiation induction. This may be the reason why only PEG-DET and DET achieved differentiation induction.

Incidentally, the above-mentioned differentiation induction was reproduced also in an in vivo experiment of Runx 2 gene introduction by PEG-DET (N/P=80), in which it was confirmed that bone regeneration at bone-defect area had been promoted.

Example 6

Titration of PEG-DET

Figure 7:
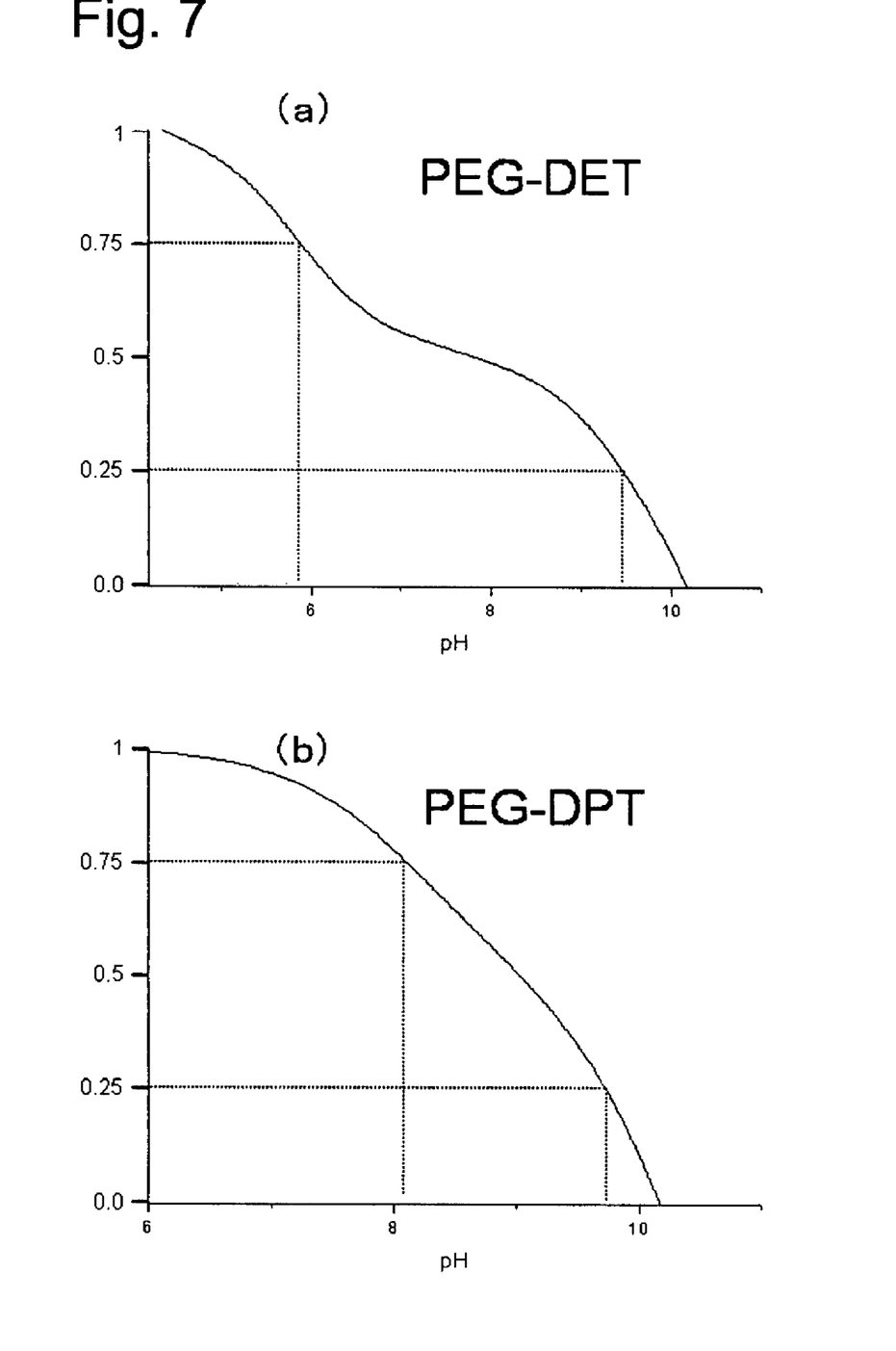
In FIG. 7, (a) is a graph of pH-α curve of PEG-DET, and (b) is a graph of pH-α curve of PEG-DPT, each in the presence of 150 mM sodium chloride in Example 6.

In 50 ml of 0.01 N aqueous solution of hydrochloric acid (+150 M sodium chloride), 30 mg of PEG-DET was dissolved. To the resultant solution, 0.01 N aqueous solution of sodium hydroxide (+150 mM sodium chloride) was added dropwise with an automatic titrator (TITSTATION TS-200 by Hirayama), and, thus, titration was conducted. Each drop had a volume of 0.063 ml. Attention was paid so that no additional drop might be added until pH had been stabilized (until at least 30 seconds had passed). From thus obtained results, pH-α curve was formed. FIG. 7-(a) is a pH-α curve for PEG-DET. Definite two-stage protonation behaviour was observed. Said two stages had a pKa values of about 6 and about 9.5. At a physiological condition of pH 7.4, ethylenediamine unit on polymer side chain is considered to be in a mono-protonated state, and to presumably take a gauche structure as indicated in the middle of the drawings below. When pH lowers down to about 5.0, said unit is considered to become di-protonated, and to take a trans structure as indicated in the left end of the drawings below. This change is considered to induce proton sponge effect.

A similar experiment was conducted also with regard to PEG-DPT as synthesized in Production Example 3, and, thus, pH-α curve was formed. As shown in FIG. 7-(b), protonation of PEG-DPT has already progressed considerably beyond mono-protonated state at pH 7.4. Thus, PEG-DPT is not considered to function as effectively as PEG-DET with respect to proton sponge effect.

<Summary>

It has proved evident that PEG-DET and DET, when forming a complex with pDNA, are polymers which show a very high ability to introduce gene into cells. Under a condition that this high ability of gene introduction was shown, cytotoxicity was very low, and, furthermore, good gene introduction was exhibited even for primary cultured cell lines into which gene introduction is usually hard. Moreover, gene expression can be maintained for a long period of time, and, thus, it has been confirmed that the above-mentioned polymers function very effectively for gene introduction for the purpose of differentiation induction of cells.

INDUSTRIAL APPLICABILITY

The present invention has thus turned out to be a practically very good system as a method for introducing gene into cells which has low toxicity and enables time-wise regulation of gene expression. For the purpose of clinical application of a therapy with use of gene introduction, the control of the state of expression of introduced gene is a very important factor since it enables efficient production of therapeutic effects and secures the safety of the therapy. Thus, the polymer of this invention is very useful as a clinically applicable gene delivery system which is necessary for the remedy of diseases with use of gene introduction.

This invention is therefore applicable in the fields of medical treatment, pharmacy, supply of medicines for research and test, etc.

The invention claimed is:

1. A composition for the delivery of nucleic acid to target cells or tissues, which comprises a polycationically charged polymer as a carrier of nucleic acid and a nucleic acid, wherein the polycationically charged polymer is a polymer of formula (III) or its salt:

wherein:

$R^{10}$ denotes hydroxyl group, oxybenzyl group or a group of —NH—$R^{11}$ wherein $R^{11}$ denotes unsubstituted or substituted with a substituent selected from the group consisting of acetalized formyl group, cyano group, formyl group, carboxyl group, amino group, $C_{1-6}$ alkoxylcarbonyl group, $C_{2-7}$ acylamide group, tri (same or different)-$C_{1-6}$ alkylsiloxy group, siloxy group and silylamino group straight chain or branched $C_{1-20}$ alkyl group;

$R^{2a}$ and $R^{2b}$ independently denote methylene group or ethylene group;

$R^3$ denotes hydrogen atom, protecting group, hydrophobic group or polymerizable group;

$R^{5a}$ and $R^{5b}$ independently denote hydroxyl group, oxybenzyl group or a group of —NH—$(CH_2)_a$—X wherein a denotes an integer of 1 to 5, and X's independently denote either a residue of amine compound which contains at least one species of primary, secondary, tertiary or quaternary ammonium salt or a residue of compound other than amine, with the proviso that, among the total of $R^{5a}$ and $R^{5b}$, there are at least two —NH—$(CH_2)_a$—X groups wherein X denotes $(NH(CH_2)_2)_c$—$NH_2$ and e denotes an integer of 1 to 5;

$R^{6a}$'s independently denote hydrogen atom or a protecting group selected from the group consisting of Z-group, Boc-group, acetyl group and trifluoroacetyl group which are usually employed as a protecting group for amino group;

n denotes an integer of 2 to 5,000;

y denotes an integer of 0 to 5,000; and z denotes an integer of 0 to 5,000, with the proviso that y+z is not larger than n, wherein the recurring units in formula (III) may be present in a random order or in the specific order of the formula; and wherein an N/P ratio is 10 to 80.

2. The composition of claim 1 for the delivery of nucleic acid, wherein, among the total of $R^{5a}$ and $R^{5b}$, —NH—$(CH_2)_a$—X groups wherein X denotes $(NH(CH_2)_2)_e$—$NH_2$ and e denotes an integer of 1 to 5, account for 50% or more, and the N/P ratio is 10 to 40.

3. The composition of claim 1 for the delivery of nucleic acid, wherein, among the total of $R^{5a}$ and $R^{5b}$, —$NH_2$—$(CH_2)_z$—X groups wherein X denotes $(NH(CH_2)_2)_e$—$NH_2$ and e denotes an integer of 1 to 5, account for 85% or more, and the N/P ratio is 10 to 40.

4. The composition of claim 1 for the delivery of nucleic acid, wherein all or a part of $R^{5a}$ and $R^{5b}$ are —NH—$(CH_2)_a$—X groups wherein a is 2 or 3 and e is an integer of 1 to 3, and the N/P ratio is 10 to 40.

5. The composition of claim 4 for the delivery of nucleic acid, wherein e is 1.

6. The composition of claim 1 for the delivery of nucleic acid, wherein $R^{11}$ denotes either unsubstituted straight chain or branched $C_{1-20}$ alkyl group or straight chain or branched $C_{1-20}$ alkyl group substituted with a substituent selected from the group consisting of acetalized formyl group, cyano group, formyl group, carboxyl group, amino group, $C_{1-6}$ alkoxycarbonyl group, $C_{2-7}$ acylamide group, tri (same or different)-$C_{1-6}$ alkylsiloxy group, siloxy group and silylamino group, and the N/P ratio is 10 to 40.

7. The composition of claim 1 for the delivery of nucleic acid, wherein $R^{2a}$ and $R^{2b}$ denote methylene group, and the N/P ratio is 10 to 40.

8. The composition of claim 1 for the delivery of nucleic acid, wherein X is selected from the group consisting of:

wherein:

$X^2$ denotes hydrogen atom, $C_{1-6}$ alkyl group or amino $C_{1-6}$ alkyl group;

$R^{7a}$, $R^{7b}$ and $R^{7c}$ independently denote hydrogen atom or methyl group;

d1, d2 and d3 independently denote an integer of 1 to 5;

e1, e2 and e3 independently denote an integer of 1 to 5;

f denotes an integer of 0 to 15;

$R^{8a}$ and $R^{8b}$ independently denote hydrogen atom or protecting group selected from the group consisting of Z-group, Boc-group, acetyl group and trifluoroacetyl group which are usually employed as a protecting group for amino group; and g denotes an integer of 0 to 15, and
the N/P ratio is 10 to 40.

9. The composition of claim 1 for the delivery of nucleic acid, wherein z denotes 0 (zero), and the N/P ratio is 10 to 40.

10. The composition of claim 1 for the delivery of nucleic acid, wherein $R^3$ is selected from the group consisting of acetyl group, acryloyl group and methacryloyl group, and the N/P ratio is 10 to 40.

11. A method for the delivery of nucleic acid to target cells or tissues, comprising:

bringing a conjugate of a nucleic acid and polycationically charged polymer into contact with target cells or tissues, wherein the polycationically charged polymer is selected from the group consisting of a block copolymer of formula (I) or its salt, a block copolymer of formula (II) or its salt and a polymer of formula (III) or its salt, wherein the block copolymer of formula (I) and the block copolymer of formula (II) are:

wherein:
R$^{1a}$ and R$^{1b}$ independently denote hydrogen atom or unsubstituted or substituted straight chain or branched C$_{1-12}$ alkyl group;
L$^1$ and L$^2$ each denote a linker;
R$^{2a}$, R$^{2b}$, R$^{2c}$ and R$^{2d}$ independently denote methylene group or ethylene group;
R$^3$ denotes hydrogen atom, protecting group, hydrophobic group or polymerizable group;
R$^4$ denotes hydroxyl or a group of —NH—(CH$_2$)$_a$—X or a residue of initiator wherein a denotes an integer of 1 to 5, and X independently denote either a residue of amine compound which contains at least one species of primary, secondary, tertiary or quaternary ammonium salt or a residue of compound other than amine;
R$^{5a}$, R$^{5b}$, R$^{5c}$ and R$^{5d}$ independently denote hydroxyl group, oxybenzyl group or a group of —NH—(CH$_2$)$_a$—X wherein a denotes an integer of 1 to 5 and X independently denote either a residue of amine compound which contains at least one species of primary, secondary, tertiary or quaternary ammonium salt or a residue of compound other than amine, with the proviso that, among the total of R$^{5a}$ and R$^{5b}$ and the total of R$^{5c}$ and R$^{5d}$, there are at least two —NH—(CH$_2$)$_a$—X groups wherein X denotes (NH(CH$_2$)$_2$)$_e$—NH$_2$ and e denotes an integer of 1 to 5;
R$^{6a}$ and R$^{6b}$ independently denote hydrogen atom or protecting group selected from the group consisting of Z-group, Boc-group, acetyl group and trifluoroacetyl group which are usually employed as a protecting group for amino group;
m denotes an integer of 5 to 20,000;
n denotes an integer of 2 to 5,000;
y denotes an integer of 0 to 5,000; and
z denotes an integer of 0 to 5,000,
with the proviso that y+z is not larger than n, and
wherein the recurring units in formulas (I) and (II) may be present in a random order or in the specific order of the formulas; and
the polymer of formula (III) is:

$$R^{10}-(COCHNH)_{n-y-z}-(COR^{2a}CHNH)_y-(COCHNH)_z-R^3, \quad (III)$$
with substituents R$^{2b}$, C=O, R$^{5a}$ on the first unit; C=O, R$^{5b}$ on the second unit; (CH$_2$)$_4$, NHR$^{6a}$ on the third unit.

wherein:
R$^{10}$ denotes hydroxyl group, oxybenzyl group or a group of —NH—R$^{11}$ wherein R$^{11}$ denotes unsubstituted or substituted with a substituent selected from the group consisting of acetalized formyl group, cyano group, formyl group, carboxyl group, amino group, C$_{1-6}$ alkoxylcarbonyl group, C$_{2-7}$ acylamide group, tri (same or different)-C$_{1-6}$ alkylsiloxy group, siloxy group and silylamino group straight chain or branched C$_{1-20}$ alkyl group;
R$^{2a}$ and R$^{2b}$ independently denote methylene group or ethylene group;
R$^3$ denotes hydrogen atom, protecting group, hydrophobic group or polymerizable group;
R$^{5a}$ and R$^{5b}$ independently denote hydroxyl group, oxybenzyl group or a group of —NH—(CH$_2$)$_1$—X wherein a denotes an integer of 1 to 5 and X's independently denote either a residue of amine compound which contains at least one species of primary, secondary, tertiary or quaternary ammonium salt or a residue of compound other than amine, with the proviso that, among the total of R$^{5a}$ and R$^{5b}$ there are at least two —NH—(CH$_2$)$_a$—X groups wherein X denotes (NH(CH$_2$)$_2$)$_e$—NH$_2$ and e denotes an integer of 1 to 5;
R$^{6a}$'s independently denote hydrogen atom or protecting group selected from the group consisting of Z-group, Boc-group, acetyl group and trifluoroacetyl group which are usually employed as a protecting group for amino group;
n denotes an integer of 2 to 5,000;
v denotes an integer of 0 to 5,000; and
z denotes an integer of 0 to 5,000,
with the proviso that y+z is not larger than
wherein the recurring units in formula (III) may be present in a random order or in the specific order of the formula, and
wherein the target cells or tissues are primary cultured cell lines or cells having differentiation potency, or tissues which contain said cells.

12. The method of claim 11, wherein the polycationically charged polymer is capable of keeping a gene which has been introduced into the cells in an expressible state for several days or more.

13. The method of claim 11, wherein the polycationically charged polymer is the polymer of formula (III) or its salt.

14. The method of claim 13 wherein the target cells or tissues are in the body of an individual which needs the introduction of nucleic acid, and wherein said conjugate of nucleic acid and polycationically charged polymer is administered to said individual prior to the contact.

15. A polymer of formula (III) or its salt:

$$R^{10}-(COCHNH)_{n-y-z}-(COR^{2a}CHNH)_y-(COCHNH)_z-R^3, \quad (III)$$
with substituents R$^{2b}$, C=O, R$^{5a}$ on the first unit; C=O, R$^{5b}$ on the second unit; (CH$_2$)$_4$, NHR$^{6a}$ on the third unit.

wherein:
R$^{10}$ denotes hydroxyl group, oxybenzyl group or a group of —NH—R$^{11}$ wherein R$^{11}$ denotes unsubstituted or substituted with a substituent selected from the group consisting of acetalized formyl group, cyano group, formyl group, carboxyl group, amino group, C$_{1-6}$ alkoxylcarbonyl group, C$_{2-7}$ acylamide group, tri (same or different)-C$_{1-6}$ alkylsiloxy group, siloxy group and silylamino group straight chain or branched C$_{1-20}$ alkyl group;
R$^{2a}$ and R$^{2b}$ independently denote methylene group or ethylene group;
R$^3$ denotes hydrogen atom, protecting group, hydrophobic group or polymerizable group;
R$^{5a}$ and R$^{5b}$ independently denote hydroxyl group, oxybenzyl group or a group of —NH—(CH$_2$)$_a$—X wherein a denotes an integer of 1 to 5, and X's independently denote either a residue of amine compound which contains at least one species of primary, secondary, tertiary or quaternary ammonium salt or a residue of compound other than amine, with the proviso that, among the total of R$^{5a}$ and R$^{5b}$, there are at least two —NH—(CH$_2$)$_a$—X groups wherein X denotes (NH(CH$_2$)$_2$)$_e$—NH$_2$ and e denotes an integer of 1 to 5;

$R^{6a}$'s independently denote hydrogen atom or a protecting group selected from the group consisting of Z-group, Boc-group, acetyl group and trifluoroacetyl group which are usually employed as a protecting group for amino group;

n denotes an integer of 2 to 5,000;

y denotes an integer of 0 to 5,000; and z denotes an integer of 0 to 5,000, with the proviso that y+z is not larger than n, wherein the recurring units in formula (III) may be present in a random order or in the specific order of the formula.

16. The polymer or salt of claim 15, wherein, among the total of $R^{5a}$ and $R^{5b}$, —NH—$(CH_2)_a$—X groups wherein X denotes $(NH(CH_2)_2)_e$—$NH_2$ and e denotes an integer of 1 to 5, account for 50% or more.

17. The polymer or salt of claim 15, wherein, among the total of $R^{5a}$ and $R^{5b}$, —NH—$(CH_2)_a$—X groups wherein X denotes $(NH(CH_2)_2)_e$—$NH_2$ and e denotes an integer of 1 to 5, account for 85% or more.

18. The polymer or salt of claim 15, wherein all or a part of $R^{5a}$ and $R^{5b}$ are —NH—$(CH_2)_a$—X groups wherein a is 2 or 3 and e is an integer of 1 to 3.

19. The polymer or salt of claim 18, wherein e is 1.

20. The polymer or salt of a claim 15, wherein X is selected from the group consisting of:

-continued wherein:

$X^2$ denotes hydrogen atom, $C_{1-6}$ alkyl group or amino $C_{1-6}$ alkyl group;

$R^{7a}$, $R^{7b}$ and $R^{7c}$ independently denote hydrogen atom or methyl group;

d1, d2 and d3 independently denote an integer of 1 to 5;

e1, e2 and e3 independently denote an integer of 1 to 5;

f denotes an integer of 0 to 15;

$R^{8a}$ and $R^{8b}$ independently denote hydrogen atom or protecting group selected from the group consisting of Z-group, Boc-group, acetyl group and trifluoroacetyl group which are usually employed as a protecting group for amino group; and g denotes an integer of 0 to 15.

21. The polymer or salt of claim 15, wherein z denotes 0 (zero).

22. The polymer or salt of claim 15, wherein $R^3$ is selected from the group consisting of acetyl group, acryloyl group and methacryloyl group.

* * * * *